United States Patent [19]

Siri

[11] Patent Number: Plant 6,566

[45] **Date of Patent: * Jan. 31, 1989**

[54] MINIATURE CARNATION—DONNA

[75] Inventor: Angelo J. Siri, San Francisco, Calif.

[73] Assignee: Siri Brothers Nursery Inc., East Palo Alto, Calif.

[ * ] Notice: The portion of the term of this patent subsequent to Aug. 31, 2004 has been disclaimed.

[21] Appl. No.: 641,922

[22] Filed: Aug. 17, 1984

[51] Int. Cl.[4] ..... A01H 5/00

[52] U.S. Cl. ..... Plt./70

[58] Field of Search ..... Plt./70–72

*Primary Examiner*—Robert E. Bagwill

*Attorney, Agent, or Firm*—Limbach, Limbach & Sutton

[57] ABSTRACT

A carnation plant having medium-dark lavender blossoms with a fluorescent quality.

1 Drawing Sheet

BACKGROUND OF THE NEW PLANT

This invention comprises a new and distinct miniature carnation variety that has its own set of characteristics that set it apart from all other varieties of miniature carnations. The newly discovered variety, called "Donna," originated as a sport of Sandy, a variety on which a copending application Ser. No. 641,921 is filed.

The botanical classification of the new variety is Dainthus Caryophyllus Longicaulis. The commercial classification is Miniature Carnation. The plant takes the form of a bush.

Asexual propagation of the newly discovered miniature carnation variety has been made at Siri Brothers Nursery, Inc. at East Palo Alto, Calif., by taking cuttings. The cuttings so taken and grown have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
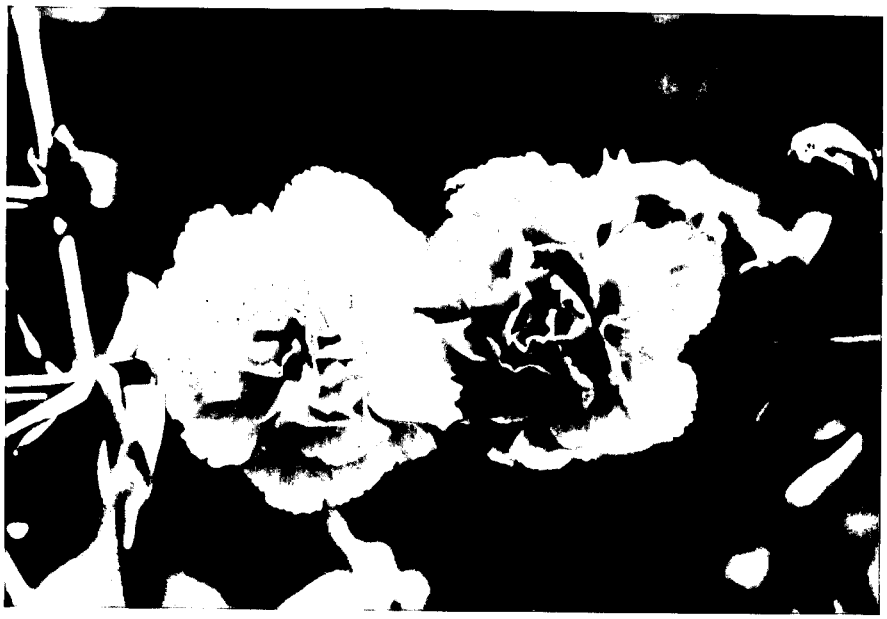
FIG. 1 PRIOR ART
FIG. 1 is an enlarged view of the bloom of the new variety Donna on the right and showing the parent Sandy on the left.
Figure 2:
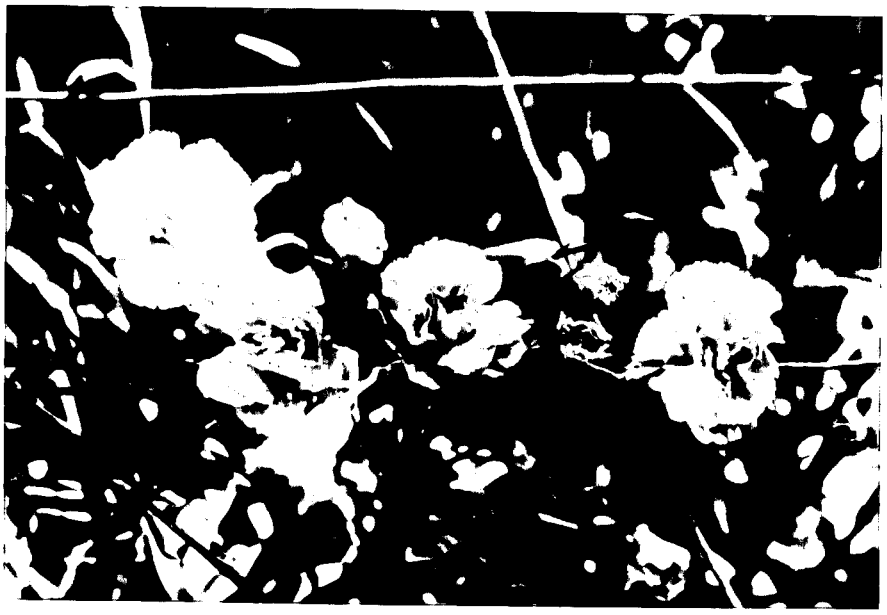
FIG. 2 PRIOR ART
FIG. 2 is a view of sprays of the new variety Donna on the right and the prior art Sandy on the left.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "R.H.S." for Royal Horticultural Colour Chart, Royal Horticultural Society, London, England.

The growth habits, foilage, stem, buds, flower size, petallage texture and edge, color stability, petal size, calyx color, and reproductive organs of this variety "Donna" are substantially identical to those of its parent "Sandy" which is the subject matter of copending application Ser. No. 641,921 and the disclosure of which is hereby incorporated by reference. Donna is distinct from Sandy by the color of the bloom.

The growth habits of Donna are generally similar to other varieties except the height tends to be short to medium, the foliage tends to be average to slightly less than average and the speed of growth tends to be fast compared to other varieties.

The foliage of Donna has a leaf size that averages 4" in length and $\frac{3}{8}$" in width. The leaf texture is smooth and leathery and the color is R.H.S. Green Group 139A with a whitish haze over the green. The leaf has one rib down the center from the base to the tip of the leaf.

The buds are oval in shape and number 4 to 5 per stem with 5 to 6 sepals per calyx, but mostly 5.

The bloom of the new variety is a medium dark lavender color that exhibits a bright fluorescent quality. The color closest to the color of the bloom as it changes year round is LC H-43 L-11. During the summer months a pale fringe appears at the edge of the petals.

The petal size has an average length of $1\frac{7}{8}$" and an average width of 1" at the widest point. The reproductive organs include a stamen of average length of 1". The number of pistils seem to vary considerably with an average length of $\frac{7}{8}$" from tip to ovary. The stigma is rounded at the very tip of the style. The ovary is ovid in shape with a length and width of approximately $\frac{3}{8}$".

Dinstinguishing Characteristics Between the New Variety and Parent

The distinguishing characteristics between the new variety and the parent is the color. The parent is a medium lavender color while the new variety is a medium dark lavender color with a fluorescent quality about it. The parent does not have this fluorescent quality.

Similar Characteristics of the New Variety and Parent

Except for the distinguishing characteristics referred to above all other characteristics are the same as the parent.

Years of asexual reproduction 1981, 1982, 1983.

I claim:

1. A new and distinct variety of miniature carnation plant, substantially as herein shown and described.

* * * * *